United States Patent
Butler et al.

(10) Patent No.: US 11,872,368 B2
(45) Date of Patent: Jan. 16, 2024

(54) SYSTEM AND METHOD FOR INDUCTIVELY CHARGING A MEDICAL DEVICE

(71) Applicant: Tandem Diabetes Care, Inc., San Diego, CA (US)

(72) Inventors: Caleb Butler, San Diego, CA (US); Robert Eastridge, San Diego, CA (US); Michael Michaud, San Diego, CA (US); Philip S. Lamb, San Diego, CA (US); Geoffrey A. Kruse, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 98 days.

(21) Appl. No.: 16/380,475

(22) Filed: Apr. 10, 2019

(65) Prior Publication Data

US 2019/0307952 A1  Oct. 10, 2019

Related U.S. Application Data

(60) Provisional application No. 62/655,516, filed on Apr. 10, 2018.

(51) Int. Cl.
*A61M 5/142* (2006.01)
*A61M 5/172* (2006.01)
(Continued)

(52) U.S. Cl.
CPC ...... *A61M 5/14244* (2013.01); *A61M 5/1723* (2013.01); *A61M 2005/14208* (2013.01);
(Continued)

(58) Field of Classification Search
CPC ...... A61M 2205/8243; A61M 5/14244; A61M 5/1723; A61M 2005/14208;
(Continued)

(56) References Cited

U.S. PATENT DOCUMENTS

| | | |
|---|---|---|
| 4,393,365 A | 7/1983 | Kondo et al. |
| 4,475,901 A | 10/1984 | Kraegen et al. |

(Continued)

FOREIGN PATENT DOCUMENTS

| | | |
|---|---|---|
| DE | 4407005 C1 | 3/1995 |
| DE | 10121317 A1 | 11/2002 |

(Continued)

OTHER PUBLICATIONS

Application and File history for U.S. Patent Application No. U.S. Appl. No. 14/317,751, filed Jun. 27, 2014 . . . Inventors: Blomquist et al.

(Continued)

*Primary Examiner* — Nathan R Price
*Assistant Examiner* — Tania Ismail
(74) *Attorney, Agent, or Firm* — Morgan, Lewis & Bockius LLP

(57) ABSTRACT

Methods and systems are disclosed wherein temperature in a device such as an ambulatory infusion pump is monitored during inductive charging of the device such that temperature-sensitive contents or components, such as, for example, insulin, particular circuitry and/or other components are not damaged. Temperature can be monitored in the device at one or more locations during inductive charging. If the temperature breaches one or more predetermined thresholds and/or is rising at a rate greater than one or more predetermined thresholds, charging can be suspended or provided at reduced power to prevent the temperature from further rising and damaging the contents and/or components of the device. One or more alerts associated with these events may also be triggered so that the user is aware of the situation and may take corrective action.

10 Claims, 3 Drawing Sheets

(51) Int. Cl.
    *G16H 20/17*     (2018.01)
    *A61N 1/378*     (2006.01)

(52) U.S. Cl.
    CPC ............ *A61M 2005/14268* (2013.01); *A61M 2205/502* (2013.01); *A61M 2205/8206* (2013.01); *A61M 2205/8243* (2013.01); *A61M 2230/201* (2013.01); *A61N 1/3787* (2013.01); *G16H 20/17* (2018.01)

(58) Field of Classification Search
    CPC .. A61M 2005/14268; A61M 2205/502; A61M 2205/8206; A61M 2230/201; A61N 1/3787; G16H 20/17; G16H 40/63
    See application file for complete search history.

(56) References Cited

U.S. PATENT DOCUMENTS

| | | | |
|---|---|---|---|
| 4,678,460 A | 7/1987 | Rosner | |
| 5,104,374 A | 4/1992 | Bishko et al. | |
| 5,122,362 A | 6/1992 | Phillips et al. | |
| 5,181,910 A | 1/1993 | Scanlon | |
| 5,311,175 A | 5/1994 | Waldman | |
| 5,338,157 A | 8/1994 | Blomquist | |
| 5,364,346 A | 11/1994 | Schrezenmeir | |
| 5,368,562 A | 11/1994 | Blomquist et al. | |
| 5,389,078 A | 2/1995 | Zalesky et al. | |
| 5,485,408 A | 1/1996 | Blomquist | |
| 5,569,186 A | 10/1996 | Lord et al. | |
| 5,641,405 A | 6/1997 | Keshaviah et al. | |
| 5,658,250 A | 8/1997 | Blomquist et al. | |
| 5,658,252 A | 8/1997 | Johnson | |
| 5,665,065 A | 9/1997 | Colman et al. | |
| 5,669,877 A | 9/1997 | Blomquist | |
| 5,685,844 A | 11/1997 | Marttila | |
| 5,690,693 A * | 11/1997 | Wang .................. | A61N 1/3787 607/61 |
| 5,695,473 A | 12/1997 | Olsen | |
| 5,713,856 A | 2/1998 | Eggers et al. | |
| 5,782,805 A | 7/1998 | Meinzer et al. | |
| 5,810,771 A | 9/1998 | Blomquist | |
| 5,814,015 A | 9/1998 | Gargano et al. | |
| 5,822,715 A | 10/1998 | Worthington et al. | |
| 5,876,370 A | 3/1999 | Blomquist | |
| 5,879,143 A | 3/1999 | Cote et al. | |
| 5,935,099 A | 8/1999 | Peterson et al. | |
| 5,935,106 A | 8/1999 | Olsen | |
| 5,997,475 A | 12/1999 | Bortz | |
| 6,024,539 A | 2/2000 | Blomquist | |
| 6,077,055 A | 6/2000 | Vilks | |
| 6,122,536 A | 9/2000 | Sun et al. | |
| 6,241,704 B1 | 6/2001 | Peterson et al. | |
| 6,248,057 B1 | 6/2001 | Mavity et al. | |
| 6,248,067 B1 | 6/2001 | Causey, III et al. | |
| 6,368,272 B1 | 4/2002 | Porumbescu | |
| 6,379,301 B1 | 4/2002 | Worthington et al. | |
| 6,422,057 B1 | 7/2002 | Anderson | |
| 6,475,180 B2 | 11/2002 | Peterson et al. | |
| 6,544,212 B2 | 4/2003 | Galley et al. | |
| 6,551,276 B1 | 4/2003 | Mann et al. | |
| 6,554,798 B1 | 4/2003 | Mann et al. | |
| 6,558,320 B1 | 5/2003 | Causey, III et al. | |
| 6,558,351 B1 | 5/2003 | Steil et al. | |
| 6,562,001 B2 | 5/2003 | Lebel et al. | |
| 6,571,128 B2 | 5/2003 | Lebel et al. | |
| 6,577,899 B2 | 6/2003 | Lebel et al. | |
| 6,582,366 B1 | 6/2003 | Porumbescu | |
| 6,641,533 B2 | 11/2003 | Causey, III et al. | |
| 6,648,821 B2 | 11/2003 | Lebel et al. | |
| 6,656,114 B1 | 12/2003 | Poulsen et al. | |
| 6,731,976 B2 | 5/2004 | Penn et al. | |
| 6,740,072 B2 | 5/2004 | Starkweather et al. | |
| 6,744,350 B2 | 6/2004 | Blomquist | |
| 6,790,198 B1 | 9/2004 | White et al. | |
| 6,809,653 B1 | 10/2004 | Mann et al. | |
| 6,835,175 B1 | 12/2004 | Porumbescu | |
| 6,852,104 B2 | 2/2005 | Blomquist | |
| 6,862,466 B2 | 3/2005 | Ackerman | |
| 6,872,200 B2 | 3/2005 | Mann et al. | |
| 6,873,268 B2 | 3/2005 | Lebel et al. | |
| 6,934,220 B1 | 8/2005 | Cruitt et al. | |
| 6,936,029 B2 | 8/2005 | Mann et al. | |
| 6,958,705 B2 | 10/2005 | Lebel et al. | |
| 6,974,437 B2 | 12/2005 | Lebel et al. | |
| 6,979,326 B2 | 12/2005 | Mann et al. | |
| 6,997,920 B2 | 2/2006 | Mann et al. | |
| 6,998,387 B1 | 2/2006 | Goke et al. | |
| 7,025,743 B2 | 4/2006 | Mann et al. | |
| 7,033,338 B2 | 4/2006 | Vilks et al. | |
| 7,041,082 B2 | 5/2006 | Blomquist et al. | |
| 7,098,803 B2 | 8/2006 | Mann et al. | |
| 7,107,706 B1 | 9/2006 | Bailey, Sr. et al. | |
| 7,109,878 B2 | 9/2006 | Mann et al. | |
| 7,136,701 B2 | 11/2006 | Greatbatch et al. | |
| 7,137,951 B2 | 11/2006 | Pilarski | |
| 7,179,226 B2 | 2/2007 | Crothall et al. | |
| 7,200,504 B1 | 4/2007 | Fister | |
| 7,258,864 B2 | 8/2007 | Clark | |
| 7,267,665 B2 | 9/2007 | Steil et al. | |
| 7,276,057 B2 | 10/2007 | Gerber | |
| 7,278,983 B2 | 10/2007 | Ireland et al. | |
| 7,282,029 B1 | 10/2007 | Poulsen et al. | |
| 7,291,107 B2 | 11/2007 | Hellwig et al. | |
| 7,307,245 B2 | 12/2007 | Faries, Jr. et al. | |
| 7,324,012 B2 | 1/2008 | Mann et al. | |
| 7,341,577 B2 | 3/2008 | Gill | |
| 7,354,420 B2 | 4/2008 | Steil et al. | |
| 7,399,277 B2 | 7/2008 | Saidara et al. | |
| 7,402,153 B2 | 7/2008 | Steil et al. | |
| 7,404,796 B2 | 7/2008 | Ginsberg | |
| 7,440,806 B1 | 10/2008 | Whitehurst et al. | |
| 7,481,759 B2 | 1/2009 | Whitehurst et al. | |
| 7,493,171 B1 | 2/2009 | Whitehurst et al. | |
| 7,515,060 B2 | 4/2009 | Blomquist | |
| 7,517,530 B2 | 4/2009 | Clark | |
| 7,556,841 B2 | 7/2009 | Kimball et al. | |
| 7,558,629 B2 | 7/2009 | Keimel et al. | |
| 7,559,926 B1 | 7/2009 | Blischak | |
| 7,572,789 B2 | 8/2009 | Cowen et al. | |
| 7,651,845 B2 | 1/2010 | Doyle, III et al. | |
| 7,678,071 B2 | 3/2010 | Lebel et al. | |
| 7,704,226 B2 | 4/2010 | Mueller, Jr. et al. | |
| 7,704,227 B2 | 4/2010 | Moberg et al. | |
| 7,715,893 B2 | 5/2010 | Kamath et al. | |
| 7,734,323 B2 | 6/2010 | Blomquist et al. | |
| 7,751,907 B2 | 7/2010 | Blomquist | |
| 7,806,886 B2 | 10/2010 | Kanderian, Jr. et al. | |
| 7,831,310 B2 | 11/2010 | Lebel et al. | |
| 7,869,851 B2 | 1/2011 | Hellwig et al. | |
| 7,912,674 B2 | 3/2011 | Killoren Clark et al. | |
| 7,935,076 B2 | 5/2011 | Estes et al. | |
| 7,959,598 B2 | 6/2011 | Estes | |
| 7,972,296 B2 | 7/2011 | Braig et al. | |
| 7,981,034 B2 | 7/2011 | Jennewine et al. | |
| 7,988,630 B1 | 8/2011 | Osorio et al. | |
| 8,030,802 B2 | 10/2011 | Lindegger et al. | |
| 8,082,041 B1 | 12/2011 | Radziemski | |
| 8,100,852 B2 | 1/2012 | Moberg et al. | |
| 8,119,593 B2 | 2/2012 | Richardson et al. | |
| 8,152,789 B2 | 4/2012 | Starkweather et al. | |
| 8,170,721 B2 | 5/2012 | Nickerson | |
| 8,192,394 B2 | 6/2012 | Estes et al. | |
| 8,192,395 B2 | 6/2012 | Estes et al. | |
| 8,204,729 B2 | 6/2012 | Sher | |
| 8,206,350 B2 | 6/2012 | Mann et al. | |
| 8,206,378 B1 | 6/2012 | Kalpin et al. | |
| 8,208,984 B2 | 6/2012 | Blomquist et al. | |
| 8,221,346 B2 | 7/2012 | Sakata et al. | |
| 8,226,891 B2 | 7/2012 | Sloan et al. | |
| 8,231,562 B2 | 7/2012 | Buck et al. | |
| 8,246,540 B2 | 8/2012 | Ginsberg | |
| 8,287,454 B2 | 10/2012 | Wolpert et al. | |
| 8,287,495 B2 | 10/2012 | Michaud et al. | |
| 8,326,546 B2 | 12/2012 | Stewart et al. | |

(56) References Cited

U.S. PATENT DOCUMENTS

| | | |
|---|---|---|
| 8,328,754 B2 | 12/2012 | Estes et al. |
| 8,348,886 B2 | 1/2013 | Kanderian, Jr. et al. |
| 8,348,923 B2 | 1/2013 | Kanderian, Jr. et al. |
| 8,376,943 B2 | 2/2013 | Kovach et al. |
| 8,414,523 B2 | 4/2013 | Blomquist et al. |
| 8,454,510 B2 | 6/2013 | Yodfat et al. |
| 8,457,758 B2 * | 6/2013 | Olson ............... A61M 5/14276 607/61 |
| 8,465,460 B2 | 6/2013 | Yodfat et al. |
| 8,573,027 B2 | 11/2013 | Rosinko et al. |
| 8,938,306 B2 | 1/2015 | Lebel |
| 8,986,253 B2 | 1/2015 | Lebel et al. |
| 9,259,531 B2 | 2/2016 | Kamen |
| 9,381,297 B2 | 7/2016 | Brown et al. |
| 9,889,250 B2 | 2/2018 | Blomquist et al. |
| 9,974,903 B1 | 5/2018 | Davis |
| 9,993,595 B2 | 6/2018 | Michaud et al. |
| 10,279,106 B1 | 5/2019 | Cook et al. |
| 10,279,107 B2 | 5/2019 | Michael |
| 10,357,603 B2 | 7/2019 | Michaud et al. |
| 10,438,696 B2 | 10/2019 | Shapley et al. |
| 10,777,319 B2 | 9/2020 | Shapley et al. |
| 2001/0031944 A1 | 10/2001 | Peterson et al. |
| 2001/0037217 A1 | 11/2001 | Abensour et al. |
| 2002/0002326 A1 | 1/2002 | Causey, III et al. |
| 2002/0016568 A1 | 2/2002 | Lebel |
| 2002/0019606 A1 | 2/2002 | Lebel |
| 2002/0065454 A1 | 5/2002 | Lebel et al. |
| 2002/0072733 A1 | 6/2002 | Flaherty |
| 2002/0072932 A1 | 6/2002 | Swamy |
| 2002/0096543 A1 | 7/2002 | Juselius |
| 2002/0107476 A1 | 8/2002 | Mann et al. |
| 2002/0143580 A1 | 10/2002 | Bristol et al. |
| 2002/0183693 A1 | 12/2002 | Peterson et al. |
| 2002/0193679 A1 | 12/2002 | Malave et al. |
| 2003/0032867 A1 | 2/2003 | Crothall et al. |
| 2003/0036683 A1 | 2/2003 | Kehr et al. |
| 2003/0050621 A1 | 3/2003 | Lebel et al. |
| 2003/0060765 A1 | 3/2003 | Campbell et al. |
| 2003/0065308 A1 | 4/2003 | Lebel et al. |
| 2003/0088238 A1 | 5/2003 | Poulsen et al. |
| 2003/0114836 A1 | 6/2003 | Estes et al. |
| 2003/0130616 A1 | 7/2003 | Steil et al. |
| 2003/0160683 A1 | 8/2003 | Blomquist |
| 2003/0163088 A1 | 8/2003 | Blomquist |
| 2003/0163090 A1 | 8/2003 | Blomquist et al. |
| 2003/0208113 A1 | 11/2003 | Mault et al. |
| 2003/0212364 A1 | 11/2003 | Mann et al. |
| 2003/0212379 A1 | 11/2003 | Bylund et al. |
| 2003/0225396 A1 | 12/2003 | Cartledge et al. |
| 2003/0236489 A1 | 12/2003 | Jacobson et al. |
| 2004/0015102 A1 | 1/2004 | Cummings et al. |
| 2004/0059295 A1 | 3/2004 | Cartledge et al. |
| 2004/0068230 A1 | 4/2004 | Estes et al. |
| 2004/0073095 A1 | 4/2004 | Causey, III et al. |
| 2004/0115067 A1 | 6/2004 | Rush et al. |
| 2004/0176720 A1 | 9/2004 | Kipfer |
| 2004/0180810 A1 | 9/2004 | Pilarski |
| 2004/0220517 A1 | 11/2004 | Starkweather et al. |
| 2004/0254434 A1 | 12/2004 | Goodnow et al. |
| 2005/0021006 A1 | 1/2005 | Tonnies |
| 2005/0022274 A1 | 1/2005 | Campbell et al. |
| 2005/0030164 A1 | 2/2005 | Blomquist |
| 2005/0050621 A1 | 3/2005 | Thomas |
| 2005/0060030 A1 | 3/2005 | Lashinski et al. |
| 2005/0065760 A1 | 3/2005 | Murtfeldt et al. |
| 2005/0085760 A1 | 4/2005 | Ware et al. |
| 2005/0095063 A1 | 5/2005 | Fathallah et al. |
| 2005/0137530 A1 | 6/2005 | Campbell et al. |
| 2005/0143864 A1 | 6/2005 | Blomquist |
| 2005/0171513 A1 | 8/2005 | Mann et al. |
| 2005/0177137 A1 | 8/2005 | Kipfer |
| 2005/0197553 A1 | 9/2005 | Cooper |
| 2005/0197621 A1 | 9/2005 | Poulsen et al. |
| 2005/0277872 A1 | 12/2005 | Colby, Jr. et al. |
| 2006/0001550 A1 | 1/2006 | Mann et al. |
| 2006/0014670 A1 | 1/2006 | Green et al. |
| 2006/0047192 A1 | 3/2006 | Hellwig et al. |
| 2006/0047538 A1 | 3/2006 | Condurso et al. |
| 2006/0080059 A1 | 4/2006 | Stupp et al. |
| 2006/0122577 A1 | 6/2006 | Poulsen et al. |
| 2006/0132292 A1 | 6/2006 | Blomquist |
| 2006/0137695 A1 | 6/2006 | Hellwig et al. |
| 2006/0149220 A1 | 7/2006 | Ullestad et al. |
| 2006/0173406 A1 | 8/2006 | Hayes et al. |
| 2006/0173444 A1 | 8/2006 | Choy et al. |
| 2006/0202859 A1 | 9/2006 | Mastrototaro et al. |
| 2006/0224109 A1 | 10/2006 | Steil et al. |
| 2006/0253097 A1 | 11/2006 | Braig et al. |
| 2006/0264895 A1 | 11/2006 | Flanders |
| 2006/0276771 A1 | 12/2006 | Galley et al. |
| 2007/0016127 A1 | 1/2007 | Staib et al. |
| 2007/0016449 A1 | 1/2007 | Cohen et al. |
| 2007/0021733 A1 | 1/2007 | Hansen et al. |
| 2007/0033074 A1 | 2/2007 | Nitzan et al. |
| 2007/0060796 A1 | 3/2007 | Kim |
| 2007/0060871 A1 | 3/2007 | Istoc et al. |
| 2007/0061735 A1 | 3/2007 | Hoffberg et al. |
| 2007/0066956 A1 | 3/2007 | Finkel |
| 2007/0100222 A1 | 5/2007 | Mastrototaro et al. |
| 2007/0106135 A1 | 5/2007 | Sloan et al. |
| 2007/0112299 A1 | 5/2007 | Smit et al. |
| 2007/0124002 A1 | 5/2007 | Estes et al. |
| 2007/0156033 A1 | 7/2007 | Causey, III et al. |
| 2007/0203454 A1 | 8/2007 | Shermer et al. |
| 2007/0219480 A1 | 9/2007 | Kamen et al. |
| 2007/0219496 A1 | 9/2007 | Kamen et al. |
| 2007/0219597 A1 | 9/2007 | Kamen et al. |
| 2007/0228071 A1 | 10/2007 | Kamen et al. |
| 2007/0233051 A1 | 10/2007 | Hohl et al. |
| 2007/0239096 A1 | 10/2007 | Keenan et al. |
| 2007/0255250 A1 | 11/2007 | Moberg et al. |
| 2008/0004601 A1 | 1/2008 | Jennewine et al. |
| 2008/0017194 A1 | 1/2008 | Hassanein et al. |
| 2008/0030369 A1 | 2/2008 | Mann et al. |
| 2008/0033357 A1 | 2/2008 | Mann et al. |
| 2008/0051709 A1 | 2/2008 | Mounce et al. |
| 2008/0051714 A1 | 2/2008 | Moberg et al. |
| 2008/0071251 A1 | 3/2008 | Moubayed et al. |
| 2008/0071580 A1 | 3/2008 | Marcus et al. |
| 2008/0097289 A1 | 4/2008 | Steil et al. |
| 2008/0106431 A1 | 5/2008 | Blomquist |
| 2008/0125700 A1 | 5/2008 | Moberg et al. |
| 2008/0125701 A1 | 5/2008 | Moberg et al. |
| 2008/0147050 A1 | 6/2008 | Mann et al. |
| 2008/0172026 A1 | 7/2008 | Blomquist |
| 2008/0172027 A1 | 7/2008 | Blomquist |
| 2008/0172028 A1 | 7/2008 | Blomquist |
| 2008/0172029 A1 | 7/2008 | Blomquist |
| 2008/0172030 A1 | 7/2008 | Blomquist |
| 2008/0172031 A1 | 7/2008 | Blomquist |
| 2008/0177165 A1 | 7/2008 | Blomquist et al. |
| 2008/0183060 A1 | 7/2008 | Steil et al. |
| 2008/0206799 A1 | 8/2008 | Blomquist |
| 2008/0228056 A1 | 9/2008 | Blomquist et al. |
| 2008/0262378 A1 | 10/2008 | Gerber et al. |
| 2008/0262380 A1 | 10/2008 | Gerber et al. |
| 2008/0262878 A1 | 10/2008 | Gerber et al. |
| 2008/0269585 A1 | 10/2008 | Ginsberg |
| 2008/0281297 A1 | 11/2008 | Pesach et al. |
| 2008/0287922 A1 | 11/2008 | Panduro |
| 2008/0294024 A1 | 11/2008 | Cosentino |
| 2008/0294294 A1 | 11/2008 | Blomquist |
| 2008/0300534 A1 | 12/2008 | Blomquist |
| 2008/0300572 A1 | 12/2008 | Rankers et al. |
| 2008/0306353 A1 | 12/2008 | Douglas et al. |
| 2008/0312723 A1 | 12/2008 | Gill et al. |
| 2009/0005724 A1 | 1/2009 | Regittnig |
| 2009/0005726 A1 | 1/2009 | Jones et al. |
| 2009/0018779 A1 | 1/2009 | Cohen et al. |
| 2009/0030733 A1 | 1/2009 | Cohen et al. |
| 2009/0036753 A1 | 2/2009 | King |
| 2009/0069749 A1 | 3/2009 | Miller et al. |
| 2009/0069787 A1 | 3/2009 | Estes et al. |

(56) References Cited

U.S. PATENT DOCUMENTS

| | | |
|---|---|---|
| 2009/0088731 A1 | 4/2009 | Campbell et al. |
| 2009/0105646 A1 | 4/2009 | Hendrixson et al. |
| 2009/0112626 A1 | 4/2009 | Talbot et al. |
| 2009/0131860 A1 | 5/2009 | Nielsen |
| 2009/0131861 A1 | 5/2009 | Braig et al. |
| 2009/0150186 A1 | 6/2009 | Cohen et al. |
| 2009/0177142 A1 | 7/2009 | Blomquist et al. |
| 2009/0177147 A1 | 7/2009 | Blomquist et al. |
| 2009/0177154 A1 | 7/2009 | Blomquist |
| 2009/0212966 A1 | 8/2009 | Panduro |
| 2009/0240193 A1 | 9/2009 | Mensinger et al. |
| 2009/0254037 A1 | 10/2009 | Bryant, Jr. et al. |
| 2010/0056993 A1 | 3/2010 | Chase |
| 2010/0057043 A1 | 3/2010 | Kovatchev et al. |
| 2010/0114015 A1 | 5/2010 | Kanderian, Jr. et al. |
| 2010/0121415 A1 | 5/2010 | Skelton et al. |
| 2010/0138197 A1 | 6/2010 | Sher |
| 2010/0145262 A1 | 6/2010 | Bengtsson et al. |
| 2010/0145303 A1 | 6/2010 | Yodfat et al. |
| 2010/0152644 A1 | 6/2010 | Pesach et al. |
| 2010/0152811 A1 | 6/2010 | Flaherty |
| 2010/0156633 A1 | 6/2010 | Buck, Jr. et al. |
| 2010/0174266 A1 | 7/2010 | Estes |
| 2010/0198142 A1 | 8/2010 | Sloan et al. |
| 2010/0198520 A1 | 8/2010 | Breton et al. |
| 2010/0218132 A1 | 8/2010 | Soni et al. |
| 2010/0222765 A1 | 9/2010 | Blomquist et al. |
| 2010/0262117 A1 | 10/2010 | Magni et al. |
| 2010/0262434 A1 | 10/2010 | Shaya |
| 2010/0274592 A1 | 10/2010 | Nitzan et al. |
| 2010/0274751 A1 | 10/2010 | Blomquist |
| 2010/0292634 A1 | 11/2010 | Kircher, Jr. et al. |
| 2010/0295686 A1 | 11/2010 | Sloan et al. |
| 2010/0305545 A1 | 12/2010 | Kanderian, Jr. et al. |
| 2010/0312085 A1 | 12/2010 | Andrews et al. |
| 2010/0324382 A1 | 12/2010 | Cantwell et al. |
| 2011/0009824 A1 | 1/2011 | Yodfat et al. |
| 2011/0021898 A1 | 1/2011 | Wei et al. |
| 2011/0033833 A1 | 2/2011 | Blomquist et al. |
| 2011/0040247 A1 | 2/2011 | Mandro et al. |
| 2011/0040251 A1 | 2/2011 | Blomquist et al. |
| 2011/0046697 A1 | 2/2011 | Gerber et al. |
| 2011/0047499 A1 | 2/2011 | Mandro et al. |
| 2011/0053121 A1 | 3/2011 | Heaton |
| 2011/0054390 A1 | 3/2011 | Searle et al. |
| 2011/0058485 A1 | 3/2011 | Sloan |
| 2011/0071765 A1 | 3/2011 | Yodfat et al. |
| 2011/0092788 A1 | 4/2011 | Long et al. |
| 2011/0098548 A1 | 4/2011 | Budiman et al. |
| 2011/0106011 A1 | 5/2011 | Cinar et al. |
| 2011/0106050 A1 | 5/2011 | Yodfat et al. |
| 2011/0112505 A1 | 5/2011 | Starkweather et al. |
| 2011/0112506 A1 | 5/2011 | Starkweather et al. |
| 2011/0125095 A1 | 5/2011 | Lebel et al. |
| 2011/0160695 A1 | 6/2011 | Sigrist et al. |
| 2011/0172744 A1 | 7/2011 | Davis et al. |
| 2011/0178717 A1 | 7/2011 | Goodnow et al. |
| 2011/0190701 A1 | 8/2011 | Remde et al. |
| 2011/0196213 A1 | 8/2011 | Thukral et al. |
| 2011/0205065 A1 | 8/2011 | Strachan et al. |
| 2011/0208155 A1 | 8/2011 | Palerm et al. |
| 2011/0238033 A1 | 9/2011 | Prod et al. |
| 2011/0257591 A1 | 10/2011 | Nelson Konen |
| 2012/0041415 A1 | 2/2012 | Estes et al. |
| 2012/0059353 A1 | 3/2012 | Kovatchev et al. |
| 2012/0059673 A1 | 3/2012 | Cohen et al. |
| 2012/0078181 A1 | 3/2012 | Smith et al. |
| 2012/0184907 A1* | 7/2012 | Smith ............... A61M 5/14244 604/152 |
| 2012/0185267 A1 | 7/2012 | Kamen et al. |
| 2012/0191061 A1 | 7/2012 | Yodfat et al. |
| 2012/0191063 A1 | 7/2012 | Brauker et al. |
| 2012/0209165 A1 | 8/2012 | Degen et al. |
| 2012/0232520 A1 | 9/2012 | Sloan et al. |
| 2012/0302991 A1 | 11/2012 | Blomquist et al. |
| 2013/0046281 A1 | 2/2013 | Javitt |
| 2013/0053816 A1 | 2/2013 | Diperna et al. |
| 2013/0238048 A1* | 9/2013 | Almendinger .......... H02J 7/007 607/40 |
| 2013/0324928 A1 | 12/2013 | Kruse |
| 2013/0331790 A1 | 12/2013 | Brown et al. |
| 2014/0012511 A1 | 1/2014 | Mensinger et al. |
| 2014/0070761 A1* | 3/2014 | Labbe .................. A61N 1/3787 320/108 |
| 2014/0187890 A1 | 7/2014 | Mensinger |
| 2014/0266022 A1 | 9/2014 | Degen et al. |
| 2014/0323961 A1 | 10/2014 | Blomquist et al. |
| 2015/0196709 A1 | 7/2015 | Jacobson et al. |
| 2016/0213843 A1* | 7/2016 | Despa ............... A61M 5/14244 |
| 2016/0339172 A1 | 11/2016 | Michaud et al. |
| 2017/0049957 A1 | 2/2017 | Michaud |
| 2017/0142658 A1 | 5/2017 | Kruse |
| 2019/0190296 A1* | 6/2019 | Paralikar ........... H02J 7/007192 |

FOREIGN PATENT DOCUMENTS

| | | |
|---|---|---|
| DE | 10352456 A1 | 7/2005 |
| EP | 1102194 A2 | 5/2001 |
| EP | 1571582 A2 | 9/2005 |
| EP | 1904153 B1 | 4/2015 |
| WO | WO-0045696 A1 | 8/2000 |
| WO | WO-0074753 A1 | 12/2000 |
| WO | WO-0152727 A1 | 7/2001 |
| WO | WO-02062212 A2 | 8/2002 |
| WO | WO-2005018507 A2 | 3/2005 |
| WO | WO-2005046559 A2 | 5/2005 |
| WO | WO-2006061169 A1 | 6/2006 |
| WO | WO-2007000425 A2 | 1/2007 |
| WO | WO-2007056592 A2 | 5/2007 |
| WO | WO-2007089537 A1 | 8/2007 |
| WO | WO-2007149533 A2 | 12/2007 |
| WO | WO-2008048556 A2 | 4/2008 |
| WO | WO-2008048582 A1 | 4/2008 |
| WO | WO-2008048583 A1 | 4/2008 |
| WO | WO-2008048584 A1 | 4/2008 |
| WO | WO-2008048585 A1 | 4/2008 |
| WO | WO-2008048586 A1 | 4/2008 |
| WO | WO-2008048587 A1 | 4/2008 |
| WO | WO-2008091320 A2 | 7/2008 |
| WO | WO-2008112078 A2 | 9/2008 |
| WO | WO-2008153689 A1 | 12/2008 |
| WO | WO-2008153819 A1 | 12/2008 |
| WO | WO-2009035759 A1 | 3/2009 |
| WO | WO-2009088983 A2 | 7/2009 |
| WO | WO-2009089028 A2 | 7/2009 |
| WO | WO-2009089029 A2 | 7/2009 |
| WO | WO-2010096449 A2 | 8/2010 |

OTHER PUBLICATIONS

Search report and Written Opinion dated Jul. 15, 2019 for PCT Application No. PCT/US2019/26765, 10 pages.
Bott, et al., "Impact of Smoking on the Metabolic Action of Subcutaneous Regular Insulin in Type 2 Diabetic Patients," Horm. Metab. Res., vol. 37, 2005, pp. 445-449.
Chase, et at., "The Use of Insulin Pumps With Meal Bolus Alarms in Children With Type 1 Diabetes to Improve Glycemic Control," Diabetes Carem, vol. 29, No. 5, May 2006, pp. 1012-1015.
"Compare Insulin Pump for Diabetes," Printed from www.diabetesnet.com/diabetes-technology/insulin-pump-models.php, Jun. 18, 2009, 4 pages.
International Search Report and Written Opinion for PCT Application No. PCT/US09/00107 dated May 4, 2009, 9 pages.
Lehmann, et al., "Combining rule-based reasoning and mathematical modeling in diabetes care," Artificial Intelligence in Medicine, vol. 6, 1994, pp. 137-160.
Hildebrandt P, "Subcutaneous Absorption of Insulin in Insulin-Dependent Diavetic patients. Influence of Species Physico-Chemical properties of Insulin and Physiological factors," Danish Medical Bulletin, Aug. 1991, 10 pages.

(56) References Cited

OTHER PUBLICATIONS

Plougmann, et al., "DiasNet—a diabetes advisory system for communication and education via the internet," International Journal of Medical Informatics, vol. 64, 2001, 1 page.

Puckett, et al., "A model for multiple subcutaneous insulin injections developed from individual diabetic patient data," vol. 269, 1995, p. E1115-E1124.

Smith Medical MD Inc., "Deltec Cozmo, Personalized Insulin Pump, Starting Guide," http://web.archive.org/web/20041207133223/http://www.cozmore.com/Library/-upload/starting.sub.--guide.sub.--032004.pdf, XP002497833, Dec. 7, 2004, pp. 1-83.

Stapel E., "Converting Between Decimals, Fractions, and Percents," Purplemath, 2006, 9 pages, Available at http://www.purplemath.com/modules/percents2.htm, 2006.

Trajanoski, et al., "Pharmacokinetic Model for the Absorption of Subcutaneously Injected Soluble Insulin and Monomeric Insulin Analogues," Biomedizinische Technik, vol. 38, No. 9. Sep. 1, 1993, pp. 224-231.

Wach, et al., "Numerical Approximation of Mathematical Model for Absorption of Subcutaneously Injected Insulin," Med & Biol. Eng & comput., vol. 33, 1995, pp. 18-23.

Walsh, et al., "Diabetes Technology—Concept 1: Super Bolus, available at Diabetes Technology—Concept 1: Super Bolus" available at http://www.diabetesnet.com/diabetes.sub.--technology/super.sub.--bolus.ph-p>, Sep. 17, 2007, 3 pages.

Walsh J., et al., "Select & Test Your Correction Factor," Pumping Insulin, Fourth Edition, Chapter 13, 2006, 10 Pages.

Walsh J., et al., "Select & Test Your Basal Rates," Pumping Insulin, Fourth Edition, Chapter 11, 2006, 30 pages.

Walsh J., et al., "Select and Test Your Carb Factor," Pumping Insulin, Fourth Edition, Chapter 12, 2006, 32 pages.

Walsh J., et al., "Pumping Insulin: Everything you need for Success on a Smart insulin Pump," Torrey Pines Press, San Diego, ISBN 1-884804-86-1, 2006, 3 pages.

wikipedia.com, "Wikipedia's definition for "basal rate"," printed from wikipedia.com on Jun. 12, 2009, 1 page.

Wilinska, et al., "Insulin Kinetics in Type-1 Diabetes: Continuous and Bolus Delivery of Rapid Acting Insulin," IEEE Transactions on Biomedical Engineering, vol. 52, No. 1, Jan. 2005, pp. 3-12.

EP Application No. 19785688.3, Extended EP Search Report dated Nov. 22, 2021, 11 pages.

\* cited by examiner

SYSTEM AND METHOD FOR INDUCTIVELY CHARGING A MEDICAL DEVICE

RELATED APPLICATION

The present application claims the benefit of U.S. Provisional Application No. 62/655,516 filed Apr. 10, 2018, which is hereby incorporated herein in its entirety by reference.

TECHNICAL FIELD

The present disclosure relates to medical pumps for delivering medicament to a patient and, more specifically, to user-wearable infusion pumps for delivering medicament such as insulin to a patient.

BACKGROUND

There are many applications in academic, industrial, and medical fields that benefit from devices and methods that are capable of accurately and controllably delivering fluids, such as liquids and gases, that have a beneficial effect when administered in known and controlled quantities. Such devices and methods can be particularly useful in the medical field where treatments for many patients include the administration of a known amount of a substance at predetermined intervals.

One category of devices for delivering such fluids is that of pumps that have been developed for the administration of insulin and other medicaments for those suffering from both type I and type II diabetes. Some pumps configured as portable infusion devices can provide continuous subcutaneous medicament injection and/or infusion therapy for the treatment of diabetes. Such therapy may include, e.g., the regular and/or continuous injection or infusion of insulin into the skin of a person suffering from diabetes and offer an alternative to multiple daily injections of insulin by an insulin syringe or an insulin pen. Such pumps can be ambulatory/portable infusion pumps that are worn by the user and may use replaceable cartridges. Examples of such pumps and various features that can be associated with such pumps include those disclosed in U.S. Patent Application Publication No. 2013/0053816; U.S. Pat. Nos. 8,573,027; 8,986,253; U.S. Patent Application Publication No. 2013/0324928; U.S. Patent Application Publication No. 2013/0331790; U.S. Pat. No. 8,287,495; U.S. patent application Ser. No. 15/241,257 (filed Aug. 19, 2016); and U.S. patent application Ser. No. 15/158,125 (filed May 18, 2016), each of which is hereby incorporated herein by reference in its entirety.

Many ambulatory infusion pumps are powered by batteries that need to periodically be recharged. This is typically accomplished by inserting a connector of a cable into a port on the infusion pump (such as, e.g., a USB or similar port) that facilitates the transfer of power and/or data and plugging the other end of the cable into a wall outlet or other power source. Recently, a number of consumer devices have been developed that utilize electromagnetic induction to charge an internal battery of a device without the need for additional physical electrical connections. In such systems, a transmitting induction coil within a charging base creates an alternating electromagnetic field. When a receiving induction coil in the device is aligned with the transmitting induction coil, power is transferred to the device where it is used to charge the battery. Embodiments of portable infusion pumps that utilize inductive charging are disclosed in U.S. Patent Publication No. 2016/0339172 and U.S. patent application Ser. No. 15/868,461, each of which is hereby incorporated herein by reference in its entirety.

One of the challenges in enabling inductive charging, in particular with medical devices such as ambulatory infusion pumps, is that wireless charging can cause unwanted heating in electrically conductive materials, such as metals. This heating is caused by the electromagnetic induction of eddy currents generated in the metal. Excessive heating can become a problem particularly when the transmitting and receiving coils of the charging system are not optimally aligned. Unwanted heating can cause problems for medical devices that would not be an issue for typical consumer electronic devices such as smartphones. For example, medicaments such as insulin are temperature sensitive and can degrade and/or spoil if exposed to high temperatures. The possibility therefore exists that the insulin or other medicament in an infusion pump could spoil or otherwise be rendered ineffective or even dangerous while the device is inductively charging via such excessive heating. This possibility can be particularly troublesome if the pump user or caregiver is now aware that the insulin in the interior of the pump has been so affected, especially if no damage to the exterior of the pump or its circuitry or other internal components has been experienced.

SUMMARY

Methods and systems are disclosed wherein temperature in a device such as an ambulatory infusion pump is monitored during inductive charging of the device such that temperature-sensitive contents or components, such as, for example, insulin, particular circuitry and/or other components are not damaged. Temperature can be monitored in the device at one or more locations during inductive charging. If the temperature breaches one or more predetermined thresholds and/or is rising at a rate greater than one or more predetermined thresholds, charging can be suspended or provided at reduced power to prevent the temperature from further rising and damaging the contents and/or components of the device. One or more alerts associated with these events may also be triggered so that the user is aware of the situation and may take corrective action.

In an embodiment, a method includes detecting that an ambulatory infusion pump configured to contain a medicament and having a rechargeable battery has been placed on an inductive charging device and initiating charging of the rechargeable battery of the ambulatory infusion pump with the inductive charging device by transmitting power to the ambulatory infusion pump at a first charging rate. During charging a plurality of temperature values within the ambulatory infusion pump can be detected while power is transmitted to the ambulatory infusion pump at the first charging rate. The plurality of temperature values within the ambulatory infusion pump can be compared to a medicament sensitivity threshold temperature at which the medicament configured to be contained within the ambulatory infusion pump can become negatively affected by the temperature. If a temperature value of the plurality of temperature values within the ambulatory infusion pump is below the medicament sensitivity threshold temperature, the inductive charging device can continue to transmit power to the ambulatory infusion pump to at the first charging rate. If a temperature value of the plurality of temperature values within the ambulatory infusion pump is above the medicament sensitivity threshold temperature, the inductive charging device can reduce the first charging rate to a second charging rate lower than the first charging rate.

In an embodiment, an ambulatory infusion pump system can include an ambulatory infusion pump including a rechargeable battery and configured to contain a medicament, an inductive charging device configured to transmit power to the ambulatory infusion pump to charge the rechargeable battery of the ambulatory infusion pump and one or more processors. The system can be configured to detect that the ambulatory infusion pump has been placed on the inductive charging device and initiate charging of the rechargeable battery of the ambulatory infusion pump with the inductive charging device by transmitting power to the ambulatory infusion pump at a first charging rate. During charging a plurality of temperature values within the ambulatory infusion pump can be detected while power is transmitted to the ambulatory infusion pump at the first charging rate. The plurality of temperature values within the ambulatory infusion pump can be compared to a medicament sensitivity threshold temperature at which the medicament configured to be contained within the ambulatory infusion pump can become negatively affected by the temperature. If a temperature value of the plurality of temperature values within the ambulatory infusion pump is below the medicament sensitivity threshold temperature, the inductive charging device can continue to transmit power to the ambulatory infusion pump to at the first charging rate. If a temperature value of the plurality of temperature values within the ambulatory infusion pump is above the medicament sensitivity threshold temperature, the inductive charging device can reduce the first charging rate to a second charging rate lower than the first charging rate.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1A:
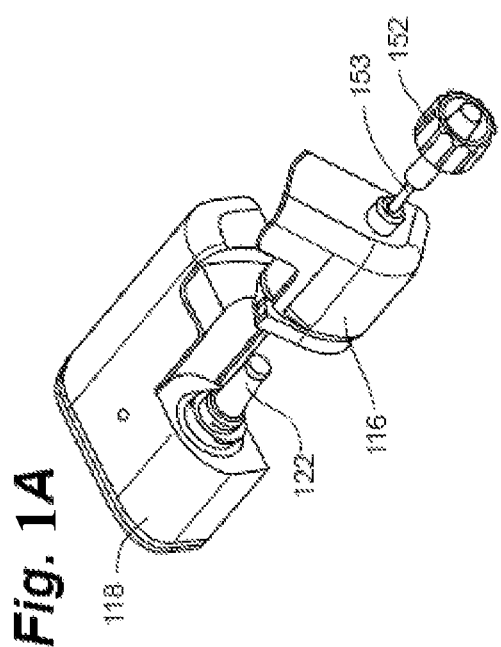
FIG. 1A-1C depict a pump system according to an embodiment of the invention.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Figure 1C:
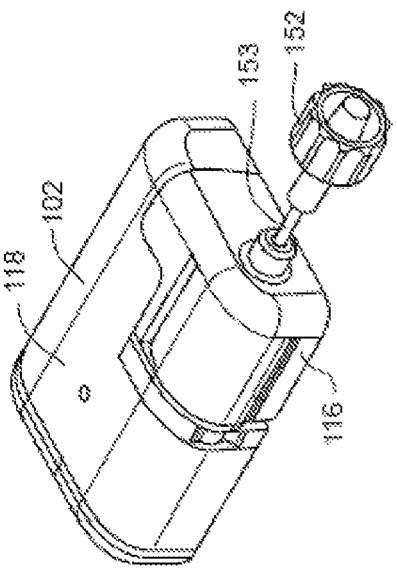
Figure 1B:
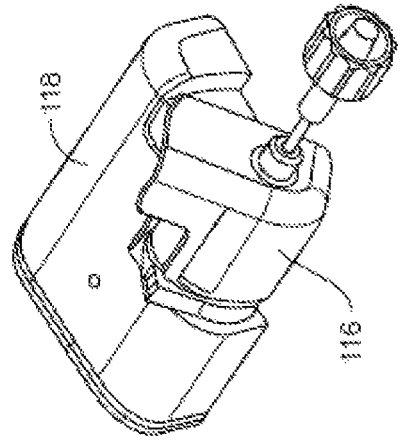

FIGS. 1A-1C depict a pump system including a pump 102 according to an embodiment of the invention. Drive unit 118 of pump 102 includes a drive mechanism 122 that mates with a recess in disposable cartridge 116 of pump 102 to attach the cartridge 116 to the drive unit 118 and provide for delivery of medicament such as insulin from the cartridge 116 to a user through a cannula. A pump system according to embodiments of the present invention can include a pump 102 including a drive unit 118 and a cartridge 116 as well as any additional components, such as for example, an infusion set. A short length of tubing 153 can extend from cartridge 116 with a connector 152 designed to attach to a corresponding connector of such an infusion set that includes a length of tubing extending from the corresponding connector to an infusion site having an infusion site connector to deliver medicament to the infusion site. Further details regarding such pumps can be found in U.S. patent application Ser. No. 14/707,851 filed May 8, 2015 and U.S. Patent Publication Nos. 2016/0339172 and 2017/0049957, each of which is hereby incorporated herein by reference in its entirety.

In one embodiment, pump 102 includes one or more processors that control operations of the pump and, in some embodiments, may receive information and/or commands from one or more separate devices. Such a separate device can include, for example, a dedicated remote control or a smartphone or other consumer electronic device executing an application configured to enable the device to transmit operating commands to the processor of pump 102. Other separate devices may include, e.g., a continuous glucose monitor (CGM), smart pen or other device designed to provide information about a user's blood glucose values or other relevant information about the user. In some embodiments, processor can also transmit information to one or more separate devices (such as, e.g., a smartphone, smartwatch, laptop or personal computer, table computer, CGM, etc.), such as information pertaining to device parameters, alarms, reminders, pump status, etc.

Figure 2C:
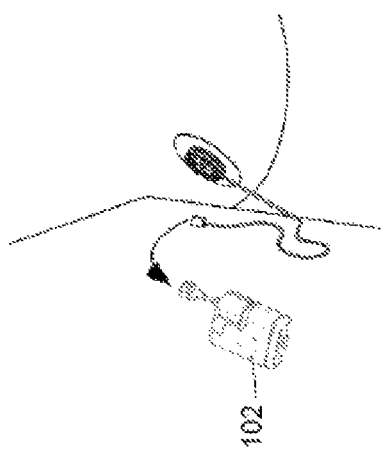
FIGS. 2A-2D depict a procedure for inductively charging a battery of a pump system according to an embodiment of the invention.
Figure 2D:
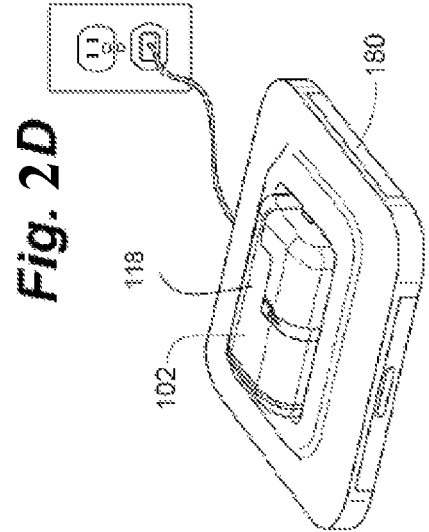
Figure 2A:
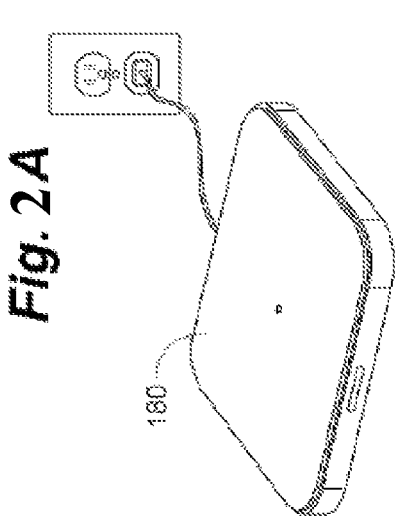
Figure 2B:
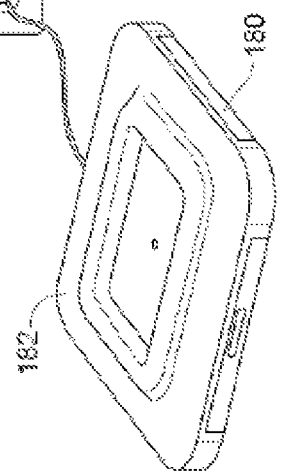

Referring to FIGS. 2A-2D, pumps according to embodiments of the present disclosure can include one or more rechargeable batteries in and/or associated with the pump drive unit 118. In some embodiments, a rechargeable battery can be inductively charged by, for example, an inductive charging pad 180. As depicted in FIG. 2B, in some embodiments, the charging pad 180 can include a cover 182 having a cutout sized to receive pump 102 in order to properly position and retain pump 102 on the charging pad 180 during recharging. In some embodiments, as shown in FIGS. 2A, 2B, 2D, the charging pad 180 may receive power by being connected to a wall outlet. In other embodiments, the charging pad 180 may additionally or alternatively include a power connection to, for example, a computer (e.g., via USB), a 12 volt automobile outlet, a battery pack (e.g., via USB), and a solar panel, among others.

To charge the pump 102, the pump 102 may first be disconnected from the tubing of the infusion set (as depicted in FIG. 2C). The pump can then be placed onto the charging pad 180 (as depicted in FIG. 2D), where its battery will automatically be inductively (re)charged when the pad 180 is connected to a power source. In another embodiment, the pump 102 can remain connected to the infusion set and the user while the battery is recharged. In some embodiments, a pump that can be inductively charged does not include a connection, such as a USB port, into which a power cord can be inserted for power transfer. Such an embodiment provides the advantages of being more robust for waterproofing because of the lack of exposed electrical contacts and obviating electrical isolation requirements imposed upon such connections.

Inductive charging of pump 102 can be carried out according to known standards, such as, for example, the Qi standard. In such a system, both the pump 102 and the charging pad 180 include an inductive coil. A transmitting coil in the charging pad 180 connected to the power source generates an oscillating magnetic field that induces an alternating current in a receiving coil in the pump 102 to transfer power to pump 102. In one embodiment, charging pad 180 is continuously or periodically (e.g., twice a second) sending an analog signal to detect the presence of a pump 102. When the pad detects the presence of a pump (via a magnetic load), it sends a digital communication signal to, e.g., a processor associated with the pump 102. The pump processor receives the signal and directs and/or sends a return signal to the pad 180, which causes the pad 180 to transmit charging power to the pump.

As noted above, such inductive charging can cause unwanted heating of devices when the batteries of those devices are charged. This issue is of particular concern with regard to devices that contain one or more heat-sensitive elements, components or contents such as medical devices including, for example, ambulatory infusion pumps that deliver one or more heat-sensitive medicaments such as insulin. Embodiments of the present invention therefore incorporate one or more temperature sensors to monitor an internal temperature in medical devices such as infusion pumps and can alter and/or suspend the inductive charging based on detected temperatures.

For example, in the case of insulin it is generally known that the critical temperature for stability of insulin is around 37 degrees Celsius. The system may therefore set a threshold temperature, such as, for example, 35 degrees Celsius, at or above which action to modify inductive charging will be taken and/or instructed to prevent the insulin from reaching 37 degrees. In one embodiment, the temperature sensor or sensors do not directly measure the temperature of the insulin or other medicament, but is/are instead located on a circuit board and measure the temperature of another element, such as a piece of metal, that directly contacts the insulin reservoir of the pump. One or more temperature sensors may in addition or alternatively be located on or near other heat-sensitive components or elements (such as, e.g., particular circuitry). The system can include an internal algorithm that converts the sensed temperature to an expected temperature of the insulin or other medicament or of the component or element of interest. Thus, when the present application refers to the system determining or measuring the temperature of the insulin or other medicament, component or element, the system may actually be measuring a temperature at a different location in the pump and converting the measurement, rather than directly measuring the temperature of the insulin or other medicament, component or element. The threshold temperature is thus directly related to a temperature that can negatively affect the medicament such as insulin, rather than a temperature that might affect the electronic or other components of the system.

The system can implement one or more of a number of procedures for preventing and/or reducing high temperatures when a temperature at or exceeding the temperature threshold is detected. There may be a single temperature sensor measuring a temperature at one location in the pump or a plurality of temperature sensors measuring temperatures in a plurality of locations. When a plurality of temperature sensors are employed, an alert may be triggered when an average of the temperature measurements exceeds a threshold or when a single temperature measurement exceeds a threshold. Temperatures may be obtained by the one or more temperature sensors and/or transmitted by the processor on a continuous basis or on a periodic basis, such as, for example, once every second, once or twice every minute, etc. Although primarily described with respect to measured temperature values exceeding a set threshold value, in some embodiments a rate of change of the measured temperature value or values can alternatively or additionally be employed in a similar fashion with respect to a threshold rate of change of temperature.

In one embodiment, when the measured temperature reaches or exceeds a preset temperature threshold (or rate of change of temperature threshold), inductive charging is disabled. This can be done by the pump sending a signal to the inductive charger to suspend charging by disabling electromagnetic power from being transmitted from the charging pad to the pump. If the pump is still connected to the user and delivering medicament, the medicament delivery can also be suspended. When the temperature has dropped to an acceptable charging level, inductive charging can be reactivated. In some embodiments, suspension of inductive charging and medicament delivery and reactivation of inductive charging can be provided in an automatic closed looped fashion. Such a closed loop system may also notify a user on a user interface of the pump and/or a remote control device of one or more of the actions taken by the system. For example, an alert may be presented on a user interface notifying the user that the inductive charging and/or insulin delivery has been suspended with a follow up alert when inductive charging and/or insulin delivery has been reinstituted. Such an alert may also include an auditory and/or vibratory notification. In a further embodiment, the system may require a user confirmation in response to one or more alerts prior to taking action, such as, for example, resuming inductive charging and/or medicament delivery.

In another embodiment, rather than completely disabling inductive charging when the system is at or above the threshold temperature (or rate of change of temperature), the system can instead lower the amount of electromagnetic power being transmitted by the charging pad (i.e. the charging rate). This can be accomplished by reducing the charging rate in the pump by a predetermined amount. The charging rate can be increased once the temperature has been lowered by a desired amount. If the pump is currently delivering medicament, in some embodiments the system can disable medicament delivery when the charging rate is reduced and resume delivery when increased charging is resumed. One or more alerts may further be provided relating to the actions taken by the system. The system can, in various embodiments, undertake one or more actions automatically or may require user confirmation before undertaking one or more actions. In some embodiments, if the temperature continues to rise or is not reduced at a desired rate and/or amount, the charging rate can be further reduced or completely disabled.

Reduced charging provides the advantage over suspending charging that the device will still be continuously charged, though the temperature will not be reduced as fast under reduced charging as when charging is completely disabled. Although reduction of the charging rate has been described as an alternative to completely suspending charging, it should be understood that these two approaches could be employed together during a single charging process, in an alternating or otherwise periodically rotating manner. For example, in one embodiment charging can be reduced if the temperature exceeds a first threshold temperature and suspended if the temperature exceeds a second, higher threshold temperature. In other embodiments, suspending charging and reducing charging may be alternated or otherwise periodically rotated, as in some instances continuous reduced charging may charge the battery faster and in other instances utilizing full power charging for periods with periods of suspended charging may charge the battery faster.

One or more additional notifications may be provided to the user by the system either concurrently with or independently of the notifications of the suspension or reduction of charging and/or other notifications described herein. For example, whether charging is intermittently disabled or the charging rate is reduced, the pump will take longer than typical to charge. The user can therefore additionally be notified that the battery may take longer than expected to charge. In addition, a high temperature and/or high rate of change of temperature may indicate improper alignment of the transmitting coil in the charging pad and receiving coil in the pump. The user may therefore alternatively or additionally be notified that there may be improper alignment and to check the alignment. Repeated temperature alarms may indicate an issue with the charging pad and therefore after a threshold number of alarms the user can be notified that the charging pad may be damaged and to replace the charging pad. In addition, when the temperature has exceeded the threshold temperature and/or reach an even higher threshold (e.g., 37 degrees Celsius for insulin), the user can be notified that the insulin or other medicament may have degraded and/or spoiled. Any of the alarms and alerts described herein can further include instructions to the user to take an action with respect to the notification. For example, in various embodiments the user can be instructed to check the alignment of the pump with respect to the charging pad, use a different charging pad, etc. in conjunction with a corresponding notification.

Detailed notifications such as those described above can be provided to the user on a user interface of a device, such as, for example, the pump, a dedicated remote controller and/or a remote consumer electronic device having a software application for controlling the pump, such as a smartphone. In addition, one or more of the pump or charging pad can include an indicator light thereon. Issues with inductive charging can alternatively or additionally be indicated by such an indicator light by, for example, the light going from off to on, the light blinking, the light blinking at a different rate, the light changing color, the light brightness changing, etc. In some embodiments, different indicator light actions (e.g., different rates of blinking) can indicate different charging issues or actions (e.g., charging suspended or charging power reduced).

Although the system is primarily described herein as suspending and/or modifying an ongoing inductive charging based on temperature measurements, there may also be circumstances where the pump is initially placed on the charger at an already elevated temperature. In such circumstances, the initial charging can be reduced, not initiated, etc. and alerts provided as described herein with respect to suspension or modification of ongoing charging.

Figure 3:
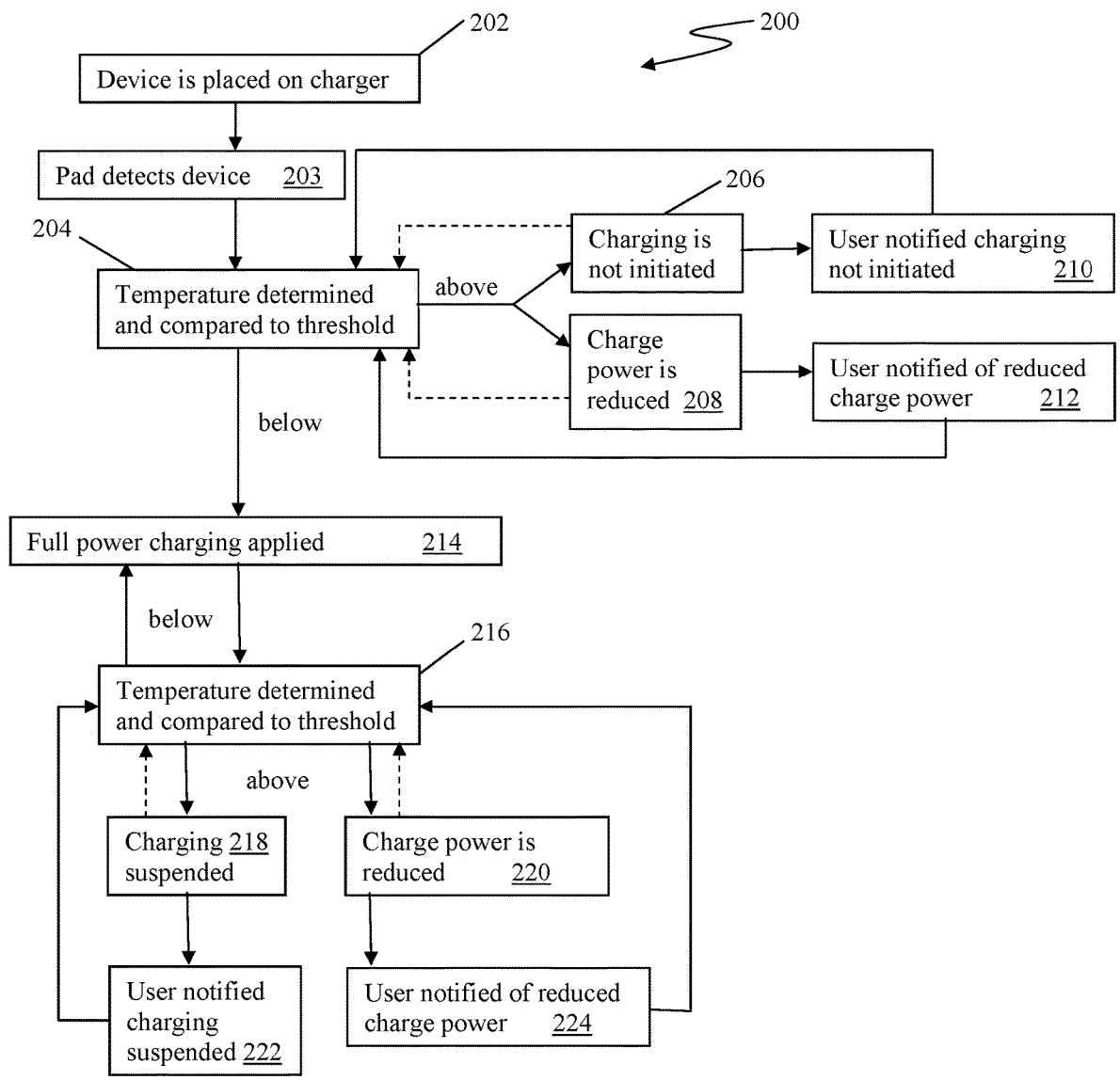
FIG. 3 depicts a flowchart of method steps for inductively charging a medical device according to embodiments of the invention.

Referring now to FIG. 3, a flowchart of methods 200 for inductively charging a medical device such as an ambulatory infusion pump that incorporates temperature monitoring is depicted. At step 202, the device is placed on the charger and the charging pad detects the device at step 203. In some embodiments, the temperature of the device is determined as described herein and compared to one or more threshold temperatures before charging is initiated at step 204. If the temperature is above a predetermined threshold, charging can alternatively not be initiated at step 206 or initiated at reduced power at step 208. With either approach, in some embodiments the user can then be notified of the action taken at step 210 or step 212. Alternatively, the corresponding action can be taken without user notification (as indicated by the dashed arrows). In various embodiments, the system can then revert to step 204 and continue to continuously or periodically monitor the temperature. If charging was reduced, upon a further increase in temperature or if the temperature is not lowering at a desired rate and/or amount, the charging may be further reduced or disabled. This may be done automatically or may be done after the user acknowledges the alert, for example.

If it is determined that the temperature is below the predetermined threshold, either initially or after clearing an alert, full power charging is initiated to charge the device at step 214. In some embodiments, the user can be notified that charging has been initiated. During charging, the temperature can be monitored and compared to a predetermined threshold, which may be the same or different from the threshold in step 204, on a periodic or continuous basis at step 216. If the temperature is below the predetermined threshold, full power charging continues and the system continues to monitor the temperature. If the temperature is above the predetermined threshold, charging can alternatively be suspended at step 218 or continued at a reduced power at step 220. The user can be notified that charging has been suspended at step 222 or reduced at step 224, respectively, and in some embodiments can further be notified that charging has been initiated (at reduced power) at step 224. Alternatively, the corresponding action can be taken without user notification (as indicated by the dashed arrows). The system can then continue to monitor the temperature at step 216, either automatically or in response to a user confirmation, and reinitiate full power charging when the temperature falls below the predetermined temperature in response to the suspended or reduced power charging. If charging was initially reduced and the temperature either continues to increase or not lowering at a desired rate and/or amount, the charging may be further reduced or disabled. The above steps can continue until the device battery is fully charged or until the device is otherwise removed from the charger.

In embodiments, the system determinations described above can all be made by a processor of the infusion pump. For example, the infusion pump can measure the temperatures, compare the temperatures and cause the inductive charger to disable and/or modulate the transmitted power by sending control signals to the pad that cause the processor of the pad to adjust the power according to the control signal. In other embodiments, one or more of these determinations can be made by a processor of the inductive charging pad or a separate device in communication with the pump, such as a remote control device.

Although the systems and methods have primarily been described herein as applying to an infusion pump for delivering a liquid medicament such as an ambulatory insulin pump, it should be understood that the systems and methods herein can be employed with any device that can utilize inductive charging to recharge an internal battery and includes one or more heat sensitive elements.

Also incorporated herein by reference in their entirety are commonly owned U.S. Pat. Nos. 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171; 9,486,571; 9,492,608; 9,503,526; 9,555,186; 9,565,718; 9,603,995; 9,669,160; 9,715,327; 9,737,656; 9,750,871; 9,867,937; 9,867,953; 9,940,441; 9,993,595; 10,016,561; 10,201,656, commonly owned U.S. Patent Publication Nos. 2009/0287180; 2012/0123230; 2013/0053816; 2014/0276419; 2014/0276423; 2014/0276569; 2014/0276570; 2015/0182693; 2016/

0082188; 2016/0339172; 2017/0049957; 2017/0142658; 2017/0182248; 2017/0250971; 2018/0021514; 2018/0071454; and 2018/0193555 and commonly owned U.S. patent application Ser. Nos. 14/707,851 and 16/266,471.

Further incorporated by reference herein in their entirety are U.S. Pat. Nos. 8,601,465; 8,502,662; 8,452,953; 8,451,230; 8,449,523; 8,444,595; 8,343,092; 8,285,328; 8,126,728; 8,117,481; 8,095,123; 7,999,674; 7,819,843; 7,782,192; 7,109,878; 6,997,920; 6,979,326; 6,936,029; 6,872,200; 6,813,519; 6,641,533; 6,554,798; 6,551,276; 6,295,506; and 5,665,065.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method, comprising:
    detecting that an ambulatory infusion pump configured to contain a medicament and having a rechargeable battery has been placed on an inductive charging device;
    initiating charging of the rechargeable battery of the ambulatory infusion pump with the inductive charging device by transmitting power to the ambulatory infusion pump at a first charging rate;
    detecting a plurality of temperature values within the ambulatory infusion pump while transmitting power to the ambulatory infusion pump at the first charging rate;
    determining a rate of change of the plurality of temperature values;
    comparing the plurality of temperature values and the rate of change of the plurality of temperature values within the ambulatory infusion pump to one or more predetermined thresholds relating to a medicament sensitivity threshold temperature, the medicament sensitivity threshold temperature being a temperature at which the medicament configured to be contained within the ambulatory infusion pump can become negatively affected by the temperature; and
    if a temperature value of the plurality of temperature values and the rate of change of the plurality of temperature values within the ambulatory infusion pump is below the one or more predetermined thresholds, causing the inductive charging device to continue to transmit power to the ambulatory infusion pump at the first charging rate, and
    if one or more of the temperature value of the plurality of temperature values and the rate of change of the plurality of temperature values within the ambulatory infusion pump is above a first threshold of the one or more predetermined thresholds and below a second threshold of the one or more predetermined thresholds higher than the first threshold, causing the inductive charging device to reduce the first charging rate to a second charging rate lower than the first charging rate, and
    if one or more of the temperature values of the plurality of temperature values and the rate of change of the plurality of temperature values within the ambulatory infusion pump is above the second threshold higher than the first threshold, causing the inductive charging device to suspend charging of the ambulatory infusion pump.

2. The method of claim 1, wherein the second charging rate is a reduced, non-zero charging rate less than the first charging rate.

3. The method of claim 1, wherein the first charging rate is a maximum charging rate that the inductive charging device can provide.

4. The method of claim 1, further comprising determining a temperature value within the ambulatory infusion pump before initiating charging of the rechargeable battery and only initiating charging if the temperature value is below the medicament sensitivity threshold temperature.

5. The method of claim 4, further comprising providing a notification to a user that charging has not been initiated if the temperature within the ambulatory infusion pump is above the medicament sensitivity threshold temperature.

6. The method of claim 1, further comprising determining a temperature value within the ambulatory infusion pump before initiating charging of the rechargeable battery and initiating charging at the second charging rate rather than the first charging rate if the temperature value is above the medicament sensitivity threshold temperature.

7. The method of claim 1, further comprising providing a notification to a user that the charging rate has been reduced to the second charging rate.

8. The method of claim 1, further comprising increasing the charging rate to the first charging rate if one of the plurality of temperatures values and the rate of change of the plurality of temperature values is below the one or more predetermined thresholds while the inductive charging device is transmitting power at the second charging rate.

9. The method of claim 1, further comprising suspending delivery of the medicament with the ambulatory infusion pump if one or more of the temperature value of the plurality of temperature values and the rate of change of the plurality of temperature values within the ambulatory infusion pump is above the one or more predetermined thresholds.

10. The method of claim 1, further comprising providing a notification to the user on a user interface of the ambulatory infusion pump or a remote control device to check alignment of the ambulatory infusion pump on the inductive charging device if one or more of the temperature value of the plurality of temperature values and the rate of change of the plurality of temperature values within the ambulatory infusion pump is above the first threshold or the second threshold.

* * * * *